United States Patent
Hecht (10) Patent No.: US 9,309,062 B2
(45) Date of Patent: Apr. 12, 2016

(54) CONVEYOR SYSTEM FOR MATERIAL SAMPLES, ESPECIALLY MEDICAL SAMPLES

(71) Applicant: GLP Systems GmbH, Hamburg (DE)

(72) Inventor: Robert Hecht, Seehausen (DE)

(73) Assignee: GLP SYSTEMS GMBH, Hamburg (DE)

( * ) Notice: Subject to any disclaimer, the term of this patent is extended or adjusted under 35 U.S.C. 154(b) by 20 days.

(21) Appl. No.: 14/378,740

(22) PCT Filed: Feb. 11, 2013

(86) PCT No.: PCT/EP2013/052706
§ 371 (c)(1),
(2) Date: Aug. 14, 2014

(87) PCT Pub. No.: WO2013/120811
PCT Pub. Date: Aug. 22, 2013

(65) Prior Publication Data
US 2015/0014125 A1    Jan. 15, 2015

(30) Foreign Application Priority Data
Feb. 15, 2012    (EP) ..................... 12155637

(51) Int. Cl.
*B65G 17/32*    (2006.01)
*G01N 35/04*    (2006.01)
*B65G 49/00*    (2006.01)

(52) U.S. Cl.
CPC ................ *B65G 49/00* (2013.01); *G01N 35/04* (2013.01); *B65G 17/32* (2013.01); *G01N 2035/0467* (2013.01); *G01N 2035/0489* (2013.01)

(58) Field of Classification Search
CPC ........... B65G 2201/0261; B65G 17/32; G01N 35/04; G01N 2035/0401; G01N 2035/046; G01N 2035/0467; Y10T 436/113332
USPC ............. 198/803.14, 867.12; 422/562, 63, 65
See application file for complete search history.

(56) References Cited

U.S. PATENT DOCUMENTS

| 6,429,016 B1 | 8/2002 | McNeil | |
| 7,314,595 B2* | 1/2008 | Honkanen | B01J 19/0046 422/552 |
| 8,211,381 B2* | 7/2012 | Ricci | B01L 9/06 422/404 |

(Continued)

FOREIGN PATENT DOCUMENTS

| DE | 4434714 | 4/1996 |
| DE | 4434714 A1 | 4/1996 |
| EP | 2074431 | 4/2011 |

*Primary Examiner* — James R Bidwell
(74) *Attorney, Agent, or Firm* — Sand & Sebolt (57) ABSTRACT

A conveying system for material samples, especially medical samples, comprising a conveyor track forming at least one conveying section and a plurality of sample holders, designed to hold one sample vessel, which are self-propelled and displaceable along the conveying section. Each sample holder comprises a drive motor, an energy accumulator for supplying the motor with driving energy, at least one fiction wheel, drivable by the motor, for transmitting a force onto the track, and a control for controlling the travels of the sample holders. Signal transmitters are arranged in the track in predetermined positions along the conveying section and are adapted to form a near-field transmission section having signal receivers arranged in the sample holders, the signal transmitters being connected to the control and adapted to transmit control data relating to the adjustment of driving parameters to the sample holders via the near-field transmission section.

20 Claims, 5 Drawing Sheets

(56) References Cited

U.S. PATENT DOCUMENTS

| | | | | |
|---|---|---|---|---|
| 8,973,736 B2 * | 3/2015 | Johns | ............... | B01D 21/262 |
| | | | | 198/439 |
| 2002/0146347 A1 | 10/2002 | McNeil | | |
| 2005/0271555 A1 | 12/2005 | Itoh | | |
| 2010/0123551 A1 | 5/2010 | Fritchie | | |
| 2010/0239461 A1 | 9/2010 | Itoh | | |

* cited by examiner

CONVEYOR SYSTEM FOR MATERIAL SAMPLES, ESPECIALLY MEDICAL SAMPLES

TECHNICAL FIELD

The invention relates to a conveyor system for material samples, especially medical samples including a conveyor track forming at least one conveyor section and a plurality of sample holders designed for holding a sample vessel each, self-propelled with adjustable drive parameters and able to be displaced along the conveyor section; each sample holder has a drive motor, an energy storage device to supply the drive motor with power and at least one friction wheel drivable by the drive motor for transferring drive power to the conveyor track; and a control system to direct the trips of the self-propelled sample holders.

PRIOR ART

In the area of analysis of material samples it is often the case that a large number of samples need to be analyzed and passed along in comparatively short periods of time. This is especially true in the area of medical samples, such as samples of body fluids that are examined using a high degree of automation in medical analysis laboratories. The laboratory receives comparatively little recompense for the examination of a single sample, therefore for reasons of cost efficiency and general economics in this area highly automated handling and processing of medical samples is required and is already being carried out today.

For this reason, it is common practice that single samples in a laboratory system are transported along a conveyor track and are brought to the prescribed analysis device arranged on the conveyor track for their respective processing. Thus the single medical samples located in the conveyor track and arranged on movable sample holders along the conveyor track are perfectly set up to undergo various analyses, either only a single such analysis or possibly even different consecutive tests. Conceivable analyses could be testing for the hemoglobin value (HB value), cholesterol, uric acid content or other medically relevant parameters in a blood sample. Urine samples could likewise be examined for pH value, content of red blood cells or general protein.

Conveyor systems comprising conveyor tracks with sample holders equipped with vessels containing samples, being transported in them have been known for a long time now. Thus there are such systems with "passive" sample holders that are moved in the conveyor track without their own drive options with the aid of conveyor devices arranged in the conveyor track, in particular conveyor belts or straps. Examples for such solutions are disclosed in DE 44 34 714 A1 and EP 2 074 431 B1.

In such conveyor systems in which the drive technology is placed in the conveyor tracks, there is the problem that in a breakdown of the drive, as a rule, the entire laboratory facility comes to a standstill and cannot be used until successful maintenance or repair of the conveyor track and its drive system has been carried out. The downtime of the entire laboratory means considerable economic loss, not least because of the throughput rates to be maintained for the laboratory's cost efficiency.

In order to avoid these losses, alternative construction possibilities could help where the drive technology is not located in the conveyor track itself but rather in the sample holders that are made to be self-propelling. An example for such a solution is shown in U.S. Pat. No. 6,429,016 B1. This discloses self-propelling sample holder robots that can be brought to their own determined place controlled by maneuverable wheels along conveyor sections in the conveyor track. The sample holder robots shown there are each constructed for receiving a plurality of sample vessels. A series of instructions are programmed for the robots in an onboard system: what action needs to be undertaken with the samples arranged on them or where these need to be taken. Then the robots run independently along the section whereby they monitor and control their trip by onboard means.

Another example for a conveyor system with sample holders traveling independently along a conveyor section in a conveyor track is disclosed in US 2005/027 1555 A1. This shows sample holders that can travel controlled from a central system via wireless communication. At the same time sensors are set in the track that register the approach of a sample holder and possibly can identify the sample put on the sample holder. The sample holders disclosed in US 2005/027 1555 A1 are each constructed for receiving a single tube-shaped sample vessel.

Although the problem of a long downtime of the conveyor system and thereby of a laboratory facility due to a defect of the drive can be overcome with the conveyor systems disclosed in U.S. Pat. No. 6,429,016 and US 2005/027 1555 A1 through placement of the drive in the sample holders themselves—instead a sample holder with a defective drive can simply be removed and replaced by a sample holder with a working drive, there are in the above-mentioned systems, as before, disadvantages and drawbacks that the present invention has made its task to overcome:

The self-propelling sample holders shown in U.S. Pat. No. 6,429,016 B1 are constructed in a very complex way concerning their control system. They have the entire "intelligence" that is required for the reliable travel of transport routes on the track. This complex construction makes the single sample holders, of which a large plurality needs to be employed in a laboratory operation, expensive to procure. Upon a breakdown of this "intelligence" onboard of only a single robot located in the track considerable errors can occur. Monitoring of all robots for their respective control and functionality is very complicated and expensive in implementation.

With the self-propelling sample holders shown in US 2005/027 1555 A1 the control system of the sample holders is clearly simpler, thereby the single sample holders are more inexpensively produced, and more robust compared with those known from the above-mentioned U.S. Pat. No. 6,429,016 B1 document, although there are still problems. In particular, communication takes place wirelessly with a central control system, thus a single remote communications remote site. This requires that a plurality of sample holders in the system is to provide a corresponding plurality of communication channels for reliable and individual transmission of data and commands to the sample holders and from the sample holders to the central control system.

DISCLOSURE OF THE INVENTION

To create a solution for this, as already mentioned, is the object of the present invention. Thus, with the invention a conveyor system for material samples, particularly medical samples, should be constructed further with self-propelling sample holders according to the known prior art, such that by a simple construction of the sample holders an efficient and rapidly reacting control of trip movements of the sample holders is possible.

This object is met by a conveyor system for material samples, particularly medical samples, wherein signal transmitters arranged along the conveyor section at predetermined positions in the conveyor track are set up for forming a near-field transmission section with signal receivers arranged in the sample holders whereby the signal transmitters are set up to be connected to the control system and for transmitting control data relating to the adjustment of the drive parameters over the near-field transmission section to the sample holders. In a further aspect a solution of the object consists of a method for operating a conveyor system for material samples including a conveyor track forming at least one conveyor section and a plurality of sample holders designed for holding a sample vessel each, self-propelled with adjustable drive parameters and able to be displaced along the conveyor section and a control system to direct the trips of the self-propelling sample holders, wherein signal transmitters arranged along the conveyor section at predetermined positions in the conveyor track for forming a near-field transmission section with signal receivers arranged in the self-propelling sample holders and connected to the control system, and the control data relating to the adjustment of drive parameters over the near-field transmission section are transmitted. Advantageous further constructions of a conveyor system according to the invention include a system wherein the signal transmitters are set up for transmitting control data regarding a drive speed to be adjusted by the sample holder. Furthermore, the signal transmitters are arranged at predetermined points of the conveyor track, particularly before or at the start of straight sections, before curves and in the area of switches. The system may further have a light path as near-field transmission section with a laser or LED as signal transmitter and a light sensor as signal receiver. The conveyor system has a data transmitting section with HF-RFID elements, particularly according to the NFC standard, as the near-field transmission section. Additionally, the conveyor system may have sample holder recognition sensors in the conveyor track for determining a sample holder located in the recognition area of such a sample holder recognition sensor. The conveyor track has switches and sensors that are arranged in travel direction before a switch in the conveyor track for recognition of an individual sample holder. Furthermore, the conveyor track may be formed from connected modular track elements arranged on a base and detachable from the base, in which the modular track elements are provided with conveyor section structures and possibly electronic components with signal transmitters and/or sensors as well as the appropriate control electronics. The modular track elements have latching means by which they are able to be detachably latched to the base, particularly being clipped onto this. The sample holders may further have collision warning sensors that are connected with the drive motor such that they stop or uncouple those upon a hindrance being detected. Signal generators are arranged in the conveyor track as signal transmitters to which corresponding signal receivers are assigned as a means for receiving signals on the sample holders, these signal receivers being set up to activate or deactivate at least one of the collision warning sensors upon signals received from the signal generators. Finally, the conveyor sections in the conveyor tack may be defined by guide grooves running across the surface of the conveyor track, and the sample holders may each have a guide pin on the underside facing the conveyor track for engaging the guide grooves.

According to the invention, a conveyor system for material samples, particularly medical samples, has a conveyor track forming at least one conveyor section and a plurality of sample holders able to be displaced along the conveyor section. These sample holders are self-propelling with adjustable drive parameters. They are also each constructed to receive one sample vessel. For the self-propulsion property each of the sample holders has a drive motor, energy storage to supply the drive motor with drive energy and at least one friction wheel drivable from the drive motor to transmit drive power to the conveyor track. The conveyor system for material samples according to the invention also has a control system to control the trips of the self-propelling sample holders. What is particular and makes up the conveyor system of the invention is founded upon signal transmitters being arranged along the conveyor section at predetermined position in the conveyor track and signal receivers being provided in the sample holders. Then, the signal transmitters are set up for the formation of a near-field transmission section with the signal receivers and connected with the control system. The signal transmitters are then set up for the transmission of the control data concerning the adjustment of drive parameters over the near-field transmission section to the self-propelling sample holders.

The design and implementation according to the invention of the transmission of control parameters or control data respectively to the self-propelling sample holders achieves two things:

First, it is not required to design the sample holders, which are made to be self-propelling, with a highly complex control system and corresponding sensor technology, which generate independently corresponding control processes by means of determined boundary conditions. In other words, the sample holders may be designed, regarding their "intelligence", comparatively simply and thereby inexpensively.

On the other hand, the invention's arrangement of signal transmitters for near-field transmission to the sample holders along the conveyor section in the conveyor track allows a transmission of control data that concerns the adjustment of parameters over a single communication channel with the respective signal transmitter. Unlike the prior art as claimed in US 2005/027 1555 A1, transmission of signals containing control commands or control data no longer occurs centrally from a single wireless transmitter to the various sample holders, which requires a distinction for communication channels, for example by an individual code series connected to each control command or even by different frequencies or the like. Rather the transmission of control data or control commands occurs along the near-field communication by means of the signal transmitters in the conveyor track that are in range of the near-field transmission with their signal receivers. Moreover, the knowledge of the sample holder's position is no longer required for the control system to output specific control data or control commands concerning drive parameters. Thus, a control command, for example, that concerns a necessary reduction of drive speed before a curve, can be transmitted to each sample holder that passes this signal transmitter by a correspondingly arranged signal transmitter before the curve, without the sample holder's position having to be known exactly in the central control system or even information for its individual assignment or recognition. Naturally, specific provisions regarding the transmission of control data can be made for the signal transmitters from the control system, for instance if a backlog occurs in a route section due to delayed further processing of a sample located on the sample holders.

The decentralized transmission of the control data concerning drive parameters by signal transmitters arranged along the conveyor route in all gives a high degree of flexibility in regard to construction of the control system and allows us to construct this system with comparatively simple means and unsusceptible to faults.

A particular example of control data transmitted with the signal transmitters are such data that concern the adjusting of travel speed. In particular, in a system according to the invention, the speed will be variable, so straight sections free of further sample holders, for example, can be comparatively quickly or speedily passed through, however before curves the speed must be reduced in order to reduce the resulting centrifugal forces and thus the danger of a possible tipping over of a sample holder or loss of material sample in the sample vessels found on the sample holder, especially if these are fluids (e.g. blood or urine).

The self-propelling sample holders must carry out speed reductions typically in the area of switches into which the conveyor route is divided, at least when they leave a straight leading travel route in the area of such a switch and are steered onto a branch line.

Control data regarding a travel speed to be adjusted by the sample holder (those that require an adjustment of speed of "0", i.e. a stop signal, are also included) are not the only control data regarding drive parameters that can be transmitted. For example, there can also be parameters in regard to travel direction, as far as the sample holders are constructed to be self-steering, or even control data in regard to the switching of sensors for travel monitoring dependent on a position along the conveyor route.

One possibility for the construction of a near-field transmission route consists of a light path in which a laser or LED can be chosen as a signal transmitter and a corresponding light sensor as a signal receiver. This light path is not necessarily one in the visible range, it can just as well be in the infrared or even the UV range. The transmission of control data along such a transmission route can occur as pulsating light flashes whose respective length and temporal sequence codes appropriate signals. It can also be coded in variable wave lengths of transmitted light. For example, data regarding a travel speed to be adjusted can be transmitted over such a light path to the sample holder as well as commands regarding the activation or deactivation of sensors or the like.

Alternatively or additionally, a data transmission route can be constructed with HF-RFID elements, particularly such according to the NFC standard, as a near-field transmission route. Over such a route relevant data may also be transmitted from the track to a sample holder traveling on this. Data transmission may easily occur in reversed direction with the aid of such elements; for this, an additional reversed arrangement of LED or laser on the sample holder and a corresponding optical receiver in the track is required. Then, over such a NFC transmission route data may also be read from the sample holder using the central control system, for example, in advance of a switch in order to match whether the travel of a currently approaching sample holder must be switched into a branch line or pass further along in the main direction. Data from the sample holder may also be transmitted over a corresponding transmission route in the direction of the central control system, for example, such as those concerning a loading condition of the energy accumulator, regarding other warning or the like so that the control system can react appropriately and provide for the sorting of a problematic sample holder at the next opportunity.

Beside the signal transmitters, sample holder recognition sensors may also be arranged in the track for determining such a sample holder located in the recognition range. Such can be arranged for example in the area of a branch line behind a switch in order to determine whether a sample holder has passed the switch and can then be switched into its normal position. An example for such a sensor can be a Hall sensor or a Reed sensor that is wired by permanent magnet arranged appropriately on a suitable place of the sample holder.

Advantageously the conveyor track constructed of modular track elements set upon a base and connected with the base in a detachable manner whereby these modular track elements have conveyor route structures and possibly electronic components with signal transmitters and/or sensors as well as the accompanying control electronics. Such modular construction allows on the one hand a simple exchange of defective track elements for new, intact elements, so for an exchange the defective track element need only be detached from the base, its electronic components, if present, are to be terminated regarding supply and data connection from the central control system, the new track element is connected to the supply and data connection by plugging in a connector, for example, and then placed detachably into the conveyor track. Moreover, it is possible to modify a conveyor track regarding possible conveyor routes by means of a modular construction of the track elements, for example, to expand these with further conveyor routes that lead to newly installed analysis devices or the like. The modular track elements advantageously have latching means by which they are detachably latched to the base, in particular being able to be clipped onto these. The base can be, for example, a metal frame or a metal plate, in particular, broken through with openings, that rests on legs or a trestle or the like in the manner of a table; the track elements can be made of plastic, for example, particularly simple of die cast plastic on which appropriate electronic components are fixed, i.e. held correspondingly in latching means, glued or screwed etc.

In another advantageous embodiment of the invention the sample holders have collision warning sensors that are connected with the drive motor in such a way that these stop or uncouple them when there is a recognized obstacle. Such collision warning sensors are a redundant safeguard so that in the case of an approach towards an unplanned, stopped sample holder in front, the oncoming sample holder stops in time, preventing the occurrence of a collision at this point. Normally, such collision should not be able to occur since the signal transmitters arranged in the conveyor track already control the movement courses of the sample holders regarding adjusting speeds and other drive parameters. However, in case the control system cannot convey the appropriate control data over the signal transmitters to the sample holders, a safeguard to prevent collisions will then take place because of the collision warning sensors. In particular, corresponding collision warning sensors face forward, that is, in the travel direction of the sample holder. Further collision warning sensors can also be arranged so that they register a lateral range, in particular in order to avoid a collision in the area of switches when there is a merging route. In order to prevent that said collision warning sensors with their sensor range hit into a lateral section with covered collision warning sensors, two travel routes going by each other closely in this section should be able to meet without danger of colliding with each other in a section of the conveyor track, in which the conveyor route has two conveyor routes running in opposite directions, in particular these collision warning sensors covering the lateral range, but another of the collision warning sensors can be specifically activated or deactivated. Corresponding signals will be conveyed advantageously over the signal transmitters to the corresponding signal receivers. For example, the collision warning sensors laterally registering a sensor area explicitly only before travel onto a switch and then only on that side from which a further string of a conveyor route approaches and will be merged with the coming branch line, can be activated and after going past the switch be deactivated again. According to the invention, this activation and deactivation takes place over a near-field transmission route as already described.

In the conveyor system according to the invention the conveyor routes in the conveyor track are advantageously provided with guide grooves across the surface of the conveyor track and the sample holders each have a guide pin on their underside for engaging into the guide grooves. Thereby the guiding and steering of the self-propelling sample holders take place through the lateral guiding of the guide pin in the guide grooves. In particular, no proper tractability of the sample holder or sample holders is then needed which leads to a simplification of the construction and thus an economical expense reduction in the production of sample holders.

A method for operating a conveyor system for material samples, particularly medical samples, which conveyor system has a conveyor track forming at least one conveyor route and a plurality of sample holders that are displaceable along the conveyor route, self-propelling with adjustable drive parameters and each receiving a sample vessel as well as a control system for controlling the travel of the self-propelling sample holders is characterized according to the invention in that the adjustment of drive parameters concerning control data is transmitted to the self-propelling sample holders over the near-field transmission route by means of a signal transmitters arranged in predetermined positions in the conveyor track along the conveyor route that are furnished for the formation of a near-field transmission route with the signal receivers in the sample holders and connected with the control system.

BRIEF DESCRIPTION OF THE DRAWINGS

Other advantages and features of the conveyor system for material samples according to the invention will ensue from the following description of an embodiment by means of the attached drawings. They are.

MEANS OF CARRYING OUT THE INVENTION

In the attached drawings an embodiment of a conveyor system of the invention is illustrated in various representations or possible forms of embodiments of the relevant components present in this system. The drawings are in no way to scale and do not necessarily show all the details. Rather they serve to illustrate the following explanation of the essential elements and features of the invention on the basis of the embodiment shown.

Figure 1:
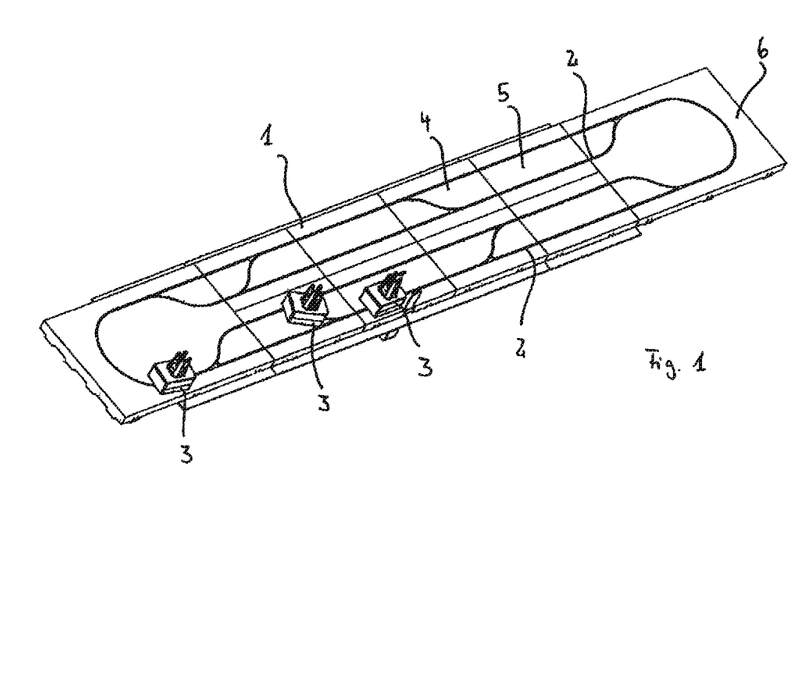
FIG. 1 shows a schematic, perspective view of a conveyor track with self-propelling sample carriers as essential components of a possible embodiment for a conveyor system of the invention.

In FIG. 1 a conveyor track 1 of a conveyor system of the invention is shown in a possible embodiment in which guide grooves 2, which define the conveyor routes, are formed on the surface of the conveyor track. These guide grooves 2 form various sections of conveyor routes, are especially connected to each other by switches and branch lines, so that various conveyor routes may be put together through shifting the switches. Self-propelling sample holders 3, here three such sample holders 3, are arranged on the guide track 1 oriented along the conveyor route. The conveyor track is constructed from various track elements, for example a track element 4 with a switch, a track element 5 with guide grooves running in a straight line and a track element 6 with switches and a U-turn.

Figure 2:
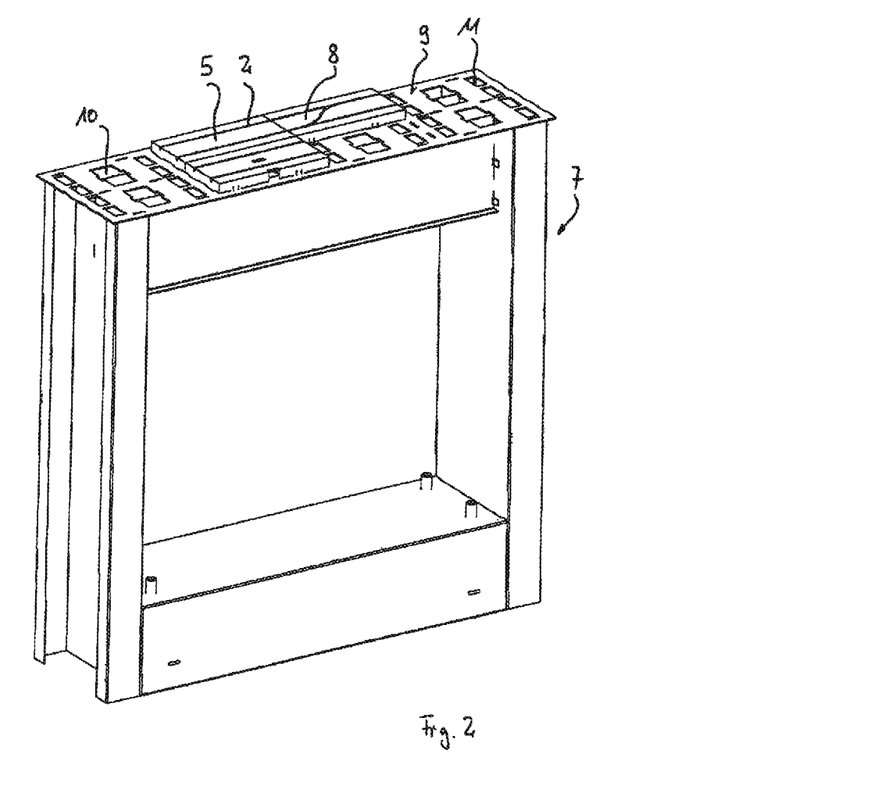
FIG. 2 is a perspective view of a base element with track elements placed upon it for the construction of a part of the conveyor track in an embodiment of the invention.

The guide track is, as particularly evident in FIG. 2, assembled from the track elements that are arranged on a base element 7 on its surface 9. In FIG. 2 a total of three track elements are represented: two track elements 8 with only straight-running guide grooves 2 and a track element 8 with a switch. The base element 7 has variously formed openings 10 and 11. The openings 11 serve for latching the track elements placed on the surface 9 of the base element 7 by which the track elements 4, 5, 6, 8 engage with the openings 11 with the corresponding latch elements 13 (see FIGS. 3 and 5) and are held there. The openings 10 are provided for passing through the power and data cables to electrical or electronic components, to be described in more detail below, placed on the bottom of the track elements opposite the guide grooves 2. For the construction of a conveyor track 1 several base elements 7 can be assembled to form an expanded base, and track elements 4, 5, 6 or 8 can be assembled as needed in order to be able to construct conveyor routes for reaching or approaching stations placed along the conveyor route, for example measuring robots etc. Also, the track elements 4, 5 and 8 can be made each with identical measurements so that, modularly exchangeable with each other, they can be placed on the surface 9 of the base element 7 and then latched into the openings 1 [sic]. On one hand, in this way a specific track, assembled with conveyor routes as needed, can be individually and simply changed, for instance if the laboratory configuration is rearranged. On the other hand, there is the possibility to simply change defective track elements, while the defective track element is removed and a working track element is installed in the resulting gap and fastened by latching. Such an exchange can occur within the shortest time. Any connections to the track element can be disconnected from the defective track element and appropriately connected to the new track element to be installed. If a defect in the track occurs, it can be repaired very quickly without a long downtimes of the entire conveyor track 1 and thus the conveyor system, with the associated disadvantages mentioned already.

Figure 3:
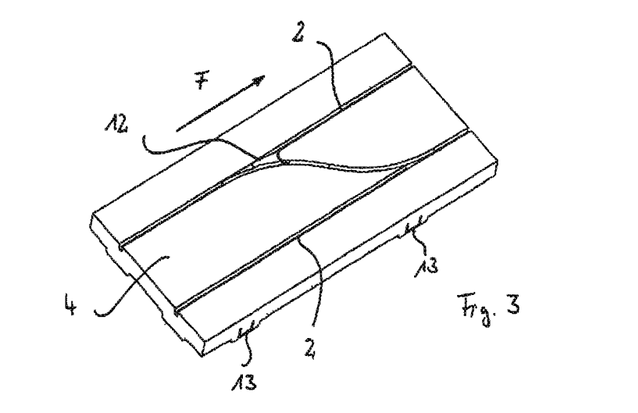
FIG. 3 is a perspective view of a track element provided with a switch.

A track element 4 is shown in enlarged view in the perspective representation of FIG. 3. This again clearly shows the latch elements 13 and the guide grooves 2 that form the conveyor route. The tack element 4 has a switch 12. A sample holder (not shown here) approaches the switch in travel direction F and, according to the switch's status, will either pass in a straight line of travel, thus on the guide groove 2 shown above in FIG. 3, or be led into the branch line on the guide groove 2 shown in FIG. 3 below.

Figure 4:
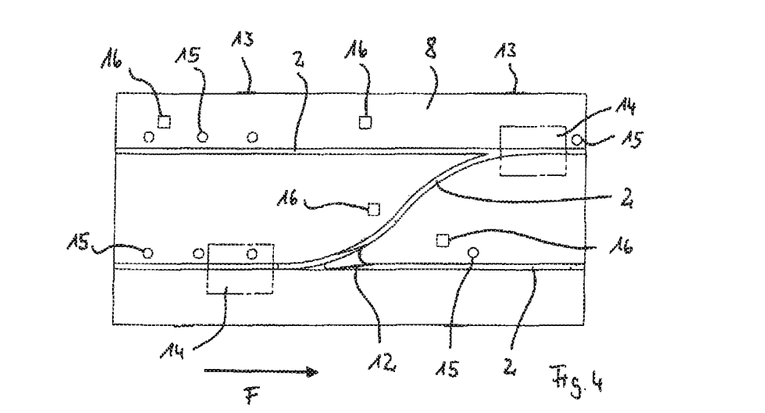
FIG. 4 is a view of another track element provided with a switch and various sensors or signal transmitters placed in the track element.

In FIG. 4 there is a view of another track element 8, which is again a track element constructed with a switch, this time in inverse construction regarding the possible transport direction. The travel direction F is marked with an arrow.

This drawing shows, according to the invention, the signal transmitters placed in the track elements as a particularity in the conveyor track, which are also present in other track elements. There are two different types of signal transmitters to identify: HR-RFID elements 14 for near-field communication according to the NFC Standard and LED's 15 that are symbolized by a small circle and by means of which signals, by means of pulsed flashes, dependent on pulse length and frequency, can be transmitted to a sample holder going over this route section, which has a corresponding receiving device for this purpose. Hall sensors are likewise placed in the track which merely serve to recognize a passing sample holder that has a permanent magnet for this purpose in a suitable position opposite the Hall sensors 16 upon passing over. The Hall sensors 16 are particularly present in the approach area to the branch line and behind the branch line 12. The placement of the Hall sensors 16 behind the switch 12 serve to detect when a sample holder has gone through the switch 12 in order to free up the switch 12 for the next pass through.

Figure 5:
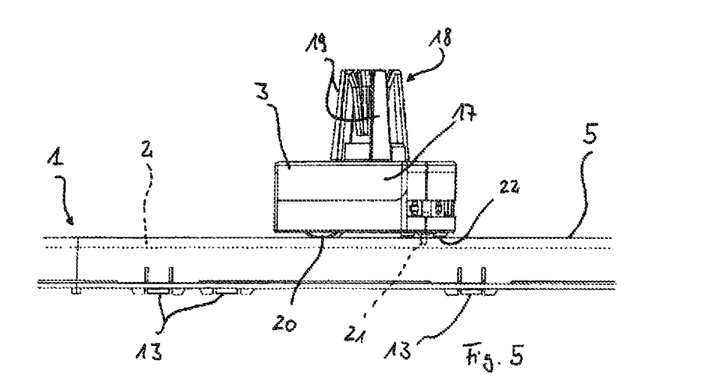
FIG. 5 is a side view of a section of a conveyor track with a self-propelling sample holder placed upon it.

FIG. 5 is a lateral representation and shows how the self-propelling sample holder 3 lies on the conveyor track 1. The self-propelling sample holder 3 has a base body 17 and a vessel receiver 18 placed on its surface for receiving a single, in essence cylindrical, in particular tubular, sample vessel (not shown here). A component of the vessel receiver 18 are four fingers 19 each placed at 90° intervals, that press upon the outer wall of the vessel and hold it in an upright position.

The sample holder 3 is driven for self-propulsion by a friction wheel 20 placed in rotation by a motor. In this embodiment the sample holder 3 has a single such friction wheel which is placed along its central axis and it rolls in the direction of this axis. The friction wheel 20 has a suitable lining with a high friction coefficient vis-à-vis the surface material of the conveyor track. Sliding elements 22 as well as guide pin 21 are placed on a side opposite the position of the friction wheel 20 in a longitudinal direction of the sample holder 3. The guide pin 21 extends, as seen in FIG. 5, into the guide groove 2 without touching the groove bottom. The interplay of guide groove 2 and guide pin 21 brings about the directional guidance of the self-propelling sample holder 3 along the conveyor route. The sliders 22 are of a low-friction material which exhibits little friction on the surface of the conveyor track 1. They are support points for the sample holder 3; the friction wheel 20 pushes the sample holder 3 sliding over the contact points of the slide elements 22 on the conveyor track 1. The central friction wheel 20 placed on the sample holder 3 has a greater width than the opening width of the groove 2, so that it can securely pass over this groove 2 without slipping off into it, and at the same time imparts enough traction when passing over this groove on the surface of the conveyor track 1.

Figure 6:
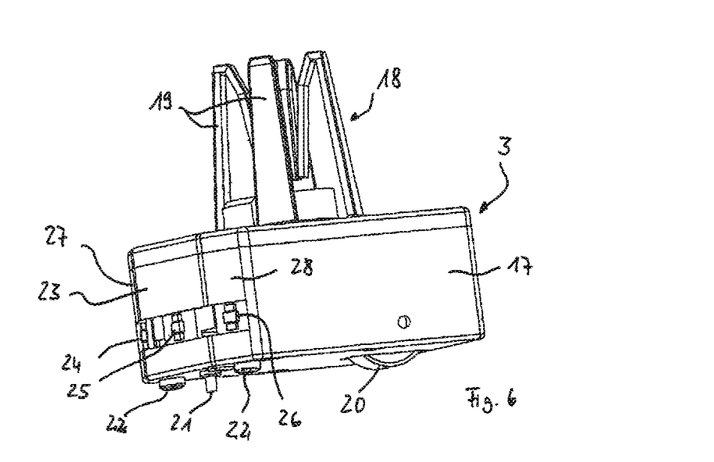
FIG. 6 is a perspective view of a self-propelling sample holder of the conveyor system of the invention.
Figure 7:
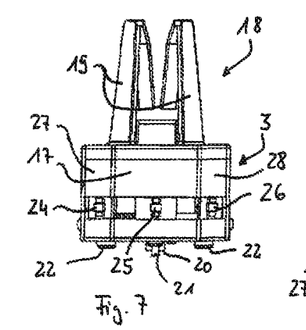
FIG. 7 is a view of the sample holder of FIG. 6 seen from above.
Figure 8:
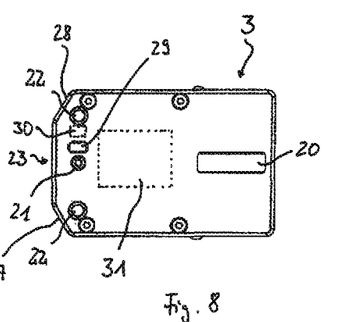
FIG. 8 is a view of the sample holder of FIG. 6 seen from below.

In FIG. 6 the sample holder 3 is seen yet again in an enlarged representation. Of particular note here is that laterally viewed bevels 27 and 28 with an incline of ca. 30° vis-à-vis the front edge, are placed on a forward end 23 which is seen situated forward in the travel direction when the sample holder is moving. In the three areas of the straight front wall and the bevels 27 and 28 thus formed, respective collision warning sensors 24, 25, 26 are placed which can recognize hindrances in the area of a sensor cone by optical signals and reflectance measurements and give appropriate signals to the motor control system of the sample holder 3. In FIG. 7 this situation is seen again in a view of the sample holder 3 from the front. FIG. 8 shows a view of the sample holder 3 from below. The bevels 27 and 28 on the front side 23 are again plain to see there. Also shown here is an optical sensor 29 that recognizes the signals emitted by the LED's 15 (shown in FIG. 4) when travelling over the conveyor track and passing them to a drive or motor control system on the sample holder 3. This optical sensor 29 forms to an extent a signal receiving device. To note further is a permanent magnet 30 placed on board the sample holder, which is placed in its position such that when travelling over the conveyor track 1 in a prescribed travel direction it sweeps over the Hall sensors 16 (cf. FIG. 4) triggering signals. There is also an HF-RFID marked with 32 for communication with the remote sites, the HF-RFID's placed in the conveyor track (cf. FIG. 4). This pairing of HF-RFID's 14 in the conveyor track and the HF-RFID's in the sample holders 3 form another pair of signal transmitters and signal receivers.

In this embodiment signals containing control data for drive parameters are transmitted to the sample holders 3 by means of LED's 15 when they travel over the LED's 15 whereby the sample holders read these signals with the optical sensor 29. Such signals are, for example, control signals regarding travel speed which the sample holder 3 needs to adjust. As an example, a command to reduce speed can be given when the sample holder 3 approaches a conveyor section shown below in FIG. 4, that is along the guide groove 2 in the figure from the left along the travel direction of the switch, and the switch is shifted for the sample holder 3 to be guided into the branch line on the guide groove 2 running above. This signal can be transmitted to the sample holder by means of the LED's 15 represented on the left in the figure. Instead of a signal transmission with pulsed or similar LED's, i.e. encryption of the signals by a single LED, several LED's with different wavelengths can be installed, of which there is only one light signal, or there can be a multicolor LED, whereby different wavelengths of the light emission can be detected by the optical sensor 29 and the different wavelengths are assigned specific control data or control commands.

Likewise in this embodiment, other control data that related to drive performance are transmitted at the same time via the LED's 15 to optical sensor 29 on sample holder 3. In particular, these are commands for switching on the collision warning sensors 24 or 26 on the bevels 27 or 28. Again in the example based on FIG. 4, to activate the collision warning sensor 26 installed on the side to the left of the direction of travel on the bevel 28, a command is transmitted by the LED's 15 in the area of the switch 12 and then to the optical sensor 29 when a sample holder 3 approaches the guide groove lying below from the left of the switch 12 along a conveyor route and should be transported on the switch into the conveyor route or guide groove lying above in the figure. The collision warning sensor 24 lying on the other bevel 27 remains deactivated. Thus, collision monitoring is carried out in the area of the branch line regarding another sample holder 3 possibly approaching there from the side and upon determining that a sample holder is present there, a stop command is issued to the drive motor. Similarly, to active the collision warning sensor 24 placed on the bevel to the right in the direction of travel, a command is given by the LED's 15 installed there for a sample holder 3 approaching from the left in the direction of travel on the upper guide groove 2, in order to be able to carry out monitoring in the direction of the entering branch line. After either going through a switch or after passing the branch line, the transmission of a control signal takes place by the LED 15 installed there to deactivate the respective collision warning sensor. For normal straight-line travel the collision warning sensors located on the bevels 27 and 28 are deactivated, as otherwise the perception of sample holder 3 located in a parallel track, for which there is no possibility of a collision, would lead to a unfounded warning and a halt of the self-propelling sample holder 3.

With near-field communication of the HF-RFIDs 14 and 31 according to the NFC standard, when the self-propelling sample holder 3 passes, data is exchanged between these two elements regarding the equipping of the respective sample holder 3 with a specific sample as well as regarding the status of the self-propelling sample holder 3 etc. Thus, the self-propelling sample holder can, for example, transmit data at these places regarding the charge status of its battery, so that a central control system, with which the individual elements, Hall sensors 16, LED's 15 and HF-RFID's are connected, can single out the sample holder 3 having a low battery charge and send it to a charge station. An exchange of data about the sample found on the sample holder 3 at critical points in the conveyor track helps to verify and carry out the choice of the correct sample holder for delivery to an analysis point.

It is self-evident that the elements LED's 15, Hall sensors 16 and HF-RFIDS's 14 are not only installed in a track element 8 as shown in FIG. 4 but in the same way or in a way suitable to the relevance of data exchange or data transmission even in other track elements, not only with switches but also for straight-line travel or in the area of turns.

Figure 9:
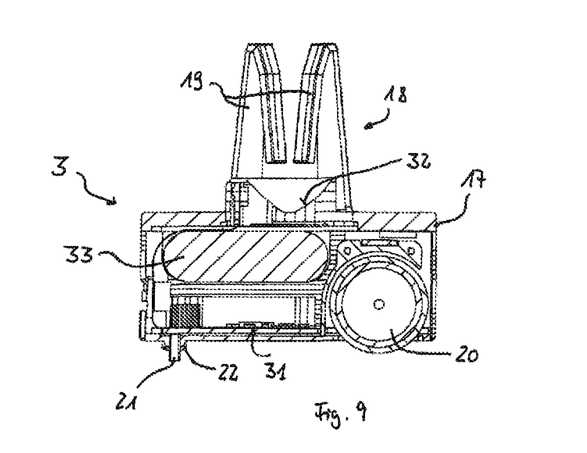
FIG. 9 is longitudinal section of the sample holder of FIG. 6.

FIG. 9 shows a longitudinal section through the sample holder 3 where the energy storage in the form of a battery 33 is seen from which the drive motor (not shown here) as well as various electrical and electronic components onboard the sample holder 3 gets its power. Further to note is a shell-like shaped bottom 32 of the vessel receiver 18 on the bottom of which an inserted vessel rests.

From the presentation of the embodiment above, the advantage of the conveyor system of the invention has yet again become clear: an advantage which results from the installation of signal transmitters at critical points of the conveyor track, which installation allows a simple and decentrally constructed and yet functioning control system of the self-propelling sample holders.

LIST OF REFERENCE NUMERALS

1 Conveyor track
2 Guide groove
3 Sample holder
4 Track element
5 Track element
6 Track element
7 Base element
8 Track element
9 Surface
10 Opening
11 Opening
12 Switch
13 Latching element
14 HF-RFID
15 LED
16 Hall sensor
17 Base body
18 Vessel receiver
19 Fingers
20 Friction wheel
21 Guide pin
22 Slide element
23 Front side
24 Collision warning sensor
25 Collision warning sensor
26 Collision warning sensor
27 Bevel
28 Bevel
29 Optical sensor
30 Magnet
31 HF-RFID
32 Bottom
33 Battery
F Travel direction

The invention claimed is:

1. A conveyor system for material samples with a conveyor track forming at least one conveyor section and a plurality of sample holders designed for holding a sample vessel, each sample holder being self-propelled with adjustable drive parameters and able to be displaced along the conveyor section, each sample holder having a drive motor, an energy storage device to supply the drive motor with power and at least one friction wheel drivable by the drive motor for transferring drive power to the conveyor track, and a control system to direct the trips of the self-propelled sample holders; wherein signal transmitters arranged along the conveyor section at predetermined positions in the conveyor track are set up and form a near-field transmission section with signal receivers arranged in the sample holders; whereby the signal transmitters are set up to be connected to the control system and transmit control data relating to the adjustment of the drive parameters over the near-field transmission section to the sample holders.

2. The conveyor system of claim 1 wherein the signal transmitters are set up for transmitting control data regarding a drive speed to be adjusted by the sample holder.

3. The conveyor system of claim 1, wherein the signal transmitters are arranged at predetermined points of the conveyor track.

4. The conveyor system of claim 1 having a light path as near-field transmission section with a laser or LED as signal transmitter and a light sensor as signal receiver.

5. The conveyor system of claim 1 having a data transmitting section with HF-RFID elements as near-field transmission section.

6. The conveyor system of claim 1 having sample holder recognition sensors in the conveyor track for determining a sample holder located in the recognition area of such a sample holder recognition sensor.

7. The conveyor system of claim 1 wherein the conveyor track has switches and sensors that are arranged in travel direction before a switch in the conveyor track for recognition of an individual sample holder.

8. The conveyor system of claim 1 wherein the conveyor track is formed from connected modular track elements arranged on a base and detachable from the base, in which the modular track elements are provided with conveyor section structures and possibly electronic components with signal transmitters and/or sensors as well as the appropriate control electronics.

9. The conveyor system of claim 8 wherein the modular track elements have latching means by which they are able to be detachably latched to the base.

10. The conveyor system of claim 1 wherein the sample holders have collision warning sensors that are connected with the drive motor such that they stop or uncouple those upon a hindrance being detected.

11. The conveyor system of claim 10 wherein signal generators are arranged in the conveyor track as signal transmitters to which corresponding signal receivers are assigned as a means for receiving signals on the sample holders, these signal receivers being set up to activate or deactivate at least one of the collision warning sensors upon signals received from the signal generators.

12. The conveyor system of claim 1 wherein conveyor sections in the conveyor tack are defined by guide grooves running across the surface of the conveyor track, and where the sample holders each have a guide pin on the underside facing the conveyor track for engaging the guide grooves.

13. A method for operating a conveyor system for material samples with a conveyor track forming at least one conveyor section and a plurality of sample holders designed for holding a sample vessel each, self-propelled with adjustable drive parameters and able to be displaced along the conveyor section and a control system to direct the trips of the self-propelling sample holders wherein signal transmitters arranged along the conveyor section at predetermined positions in the conveyor track for forming a near-field transmission section with signal receivers arranged in the self-propelling sample holders and connected to the control system, and the control data relating to the adjustment of drive parameters over the near-field transmission section are transmitted.

14. The conveying system according to claim 1, wherein the system is used to convey medical samples.

15. The conveyor system of claim 3, wherein the predetermined points of the conveyor track are before or at the start of straight sections, before curves and in the area of switches.

16. The conveyor system of claim 5, wherein the data transmitting section is in accordance with NFC standard.

17. The conveyor system of claim 9 wherein the modular track elements have latching means by which they are able to be detachably clipped to the base.

18. The method of claim 13, wherein the conveying system conveys medical samples.

19. A conveyor system for material samples with a conveyor track forming at least one conveyor section and a plurality of sample holders designed for holding a sample vessel each, self-propelled with adjustable drive parameters and able to be displaced along the conveyor section, each sample holder has a drive motor, an energy storage device to supply the drive motor with power and at least one friction wheel drivable by the drive motor for transferring drive power to the conveyor track, and a control system to direct the trips of the self-propelled sample holders wherein signal transmitters arranged along the conveyor section at predetermined positions in the conveyor track are set up for forming a near-field transmission section with signal receivers arranged in the sample holders whereby the signal transmitters are set up to be connected to the control system and for transmitting control data relating to the adjustment of the drive parameters over the near-field transmission section to the sample holders; and wherein the conveyor track is formed from connected modular track elements arranged on a base and detachable from the base, and in which the modular track elements are provided with conveyor section structures and electronic components with signal transmitters and/or sensors as well as appropriate control electronics.

20. The conveyor system of claim 19, further comprising collision warning sensors provided on the sample holders; and wherein the collision warning sensors are connected with the drive motor such that they stop or uncouple the sample holders upon a hindrance being detected.

* * * * *